US009060881B2

(12) United States Patent
Otten

(10) Patent No.: US 9,060,881 B2
(45) Date of Patent: Jun. 23, 2015

(54) LOWER LEG PROSTHESIS

(75) Inventor: Egbert Otten, Groningen (NL)

(73) Assignees: RIJKSUNIVERSITEIT GRONINGEN, Groningen (NL); ACADEMISCH ZIEKENHUIS GRONINGEN, Groningen (NL)

( * ) Notice: Subject to any disclaimer, the term of this patent is extended or adjusted under 35 U.S.C. 154(b) by 169 days.

(21) Appl. No.: 13/976,908

(22) PCT Filed: Dec. 12, 2011

(86) PCT No.: PCT/NL2011/050845
§ 371 (c)(1),
(2), (4) Date: Sep. 16, 2013

(87) PCT Pub. No.: WO2012/091555
PCT Pub. Date: Jul. 5, 2012

(65) Prior Publication Data

US 2014/0005799 A1 Jan. 2, 2014

Related U.S. Application Data

(60) Provisional application No. 61/438,272, filed on Feb. 1, 2011.

(30) Foreign Application Priority Data

Dec. 27, 2010 (EP) .................................... 10197050

(51) Int. Cl.
*A61F 2/60* (2006.01)
*A61F 2/66* (2006.01)
*A61F 2/50* (2006.01)
*A61F 2/76* (2006.01)

(52) U.S. Cl.
CPC ................ *A61F 2/60* (2013.01); *A61F 2/6607* (2013.01); *A61F 2002/5036* (2013.01); *A61F 2002/502* (2013.01); *A61F 2002/5038* (2013.01); *A61F2/604* (2013.01); *A61F 2/76* (2013.01); *A61F 2002/607* (2013.01)

(58) Field of Classification Search
CPC ................. A61F 2002/5018; A61F 2002/5036
See application file for complete search history.

(56) References Cited

U.S. PATENT DOCUMENTS 4,520,512 A 6/1985 Lehneis et al.

FOREIGN PATENT DOCUMENTS

| | | | | |
|---|---|---|---|---|
| EP | 1340478 A2 | 9/2003 | | |
| RU | 1801416 A1 * | 3/1993 | ................ | A61F 2/62 |
| RU | 2 132 665 C1 * | 7/1999 | ................ | A61F 2/66 |
| WO | 2006/118149 A1 | 11/2006 | | |

* cited by examiner

*Primary Examiner* — David H Willse
(74) *Attorney, Agent, or Firm* — Drinker Biddle & Reath LLP

(57) ABSTRACT

A lower leg prosthesis, for an amputee who has at least one leg having a leg stump, has a distal end and a proximal end. The distal end is connectable to an artificial foot. The proximal end is connectable to the leg stump via a stump socket. A use condition of the lower leg prosthesis includes the distal end being connected to the artificial foot and the proximal end being connected to the leg stump via the stump socket. The lower leg prosthesis includes a mechanism which is configured such that, in the use condition of the prosthesis and in an upright position of the amputee with the artificial foot in contact with a floor and in response to a rotative movement of the leg stump around its corresponding hip joint by the amputee with the artificial foot still in contact with the floor, the rotative movement being at least in a frontal plane of the amputee and in a first rotation direction within the frontal plane, the lower leg prosthesis rotates the artificial foot relative to the floor in a second rotation direction within the frontal plane. The first rotation direction is opposite the second rotation direction.

12 Claims, 6 Drawing Sheets

LOWER LEG PROSTHESIS

BACKGROUND

The disclosure herein relates to a lower leg prosthesis for an amputee who has at least one leg having a lower or upper leg stump. The lower leg prosthesis has a distal end, the distal end forming an artificial foot being connectable to an artificial foot. The lower leg prosthesis also has a proximal end, the proximal end forming a stump socket for connection to said leg stump, or the proximal end being connectable, optionally via an artificial knee, to a stump socket for connection to said leg stump. A use condition of the prosthesis is defined by the distal end actually being connected, if applicable, to said artificial foot, the proximal end actually being connected, if applicable, to said stump socket, and said stump socket actually being connected to said leg stump of said amputee.

Known prostheses for upper or lower leg amputees suffer from a number of drawbacks. Important drawbacks of the known prostheses are lack of balance and relatively high energy consumption during standing and walking During walking with a known prosthesis this is for example visible from the typical gait pattern, showing compensatory trunk movements by the amputee as well as a wider gait to solve balance problems in the frontal plane of the amputee. The frontal plane is the sideways plane, as distinct from the sagittal plane (fore-aft) of the amputee. Many improvements have been made on the design of prosthetic knees and feet, but only little attention has been given on the part between knee and foot, the lower leg, in order to improve lateral balance.

EP1340478A2 discloses a lower leg prosthesis of the type as initially identified hereinabove. This known prosthesis 1, shown in FIGS. 1 through 7B of EP1340478A2, includes a foot portion 3, a leg mounting portion 4 and a parallel linkage 10 connecting these portions. The leg mounting portion 4 has a flat mounting plate 4*a*. The parallel linkage 10 includes one fixed link 11 and four expansible links 13. The fixed link 11 has an upper end thereof fixed to the mounting plate 4*a* and a lower end thereof connected to the foot portion 3 via a ball joint 12. Each of the four expansible links 13 has an upper end thereof connected to the mounting plate 4*a* via an upper ball joint 14*a* and a lower end thereof connected to the foot portion 3 via a lower ball joint 14*b*.

Due to these ball joints 12, 14*a* and 14*b* and the expansibility/compressibility of the links 13, the angle of the fixed link 11 with respect to the foot portion 3 can be changed in any desired direction. In short, there are at least three degrees of freedom for the fixed link 11 and, correspondingly, for the mounting plate 4*a*. Hence, due to this high degree of freedom, an amputee wearing the known prosthesis 1 on his or her living leg stump can tilt the prosthetic lower leg in any desired direction relative to a floor while keeping the artificial foot of the prosthesis 1 resting on the floor and without rotating the artificial foot relative to the floor on which it rests. Various tilting positions of the prosthetic lower leg are shown in FIGS. 5A, 5B, 6A, 6B, 7A and 7B of EP1340478A2. In all these positions the shown artificial foot 6 has not rotated relative to the floor on which it rests due to said high degree of freedom, which in fact is more or less similar to the high degree of freedom that occurs in case of a living leg having a living ankle joint and a living foot.

Due to said high degree of freedom, also this prosthesis 1 known from EP1340478A2 suffers from the abovementioned lateral balance problems, amongst others resulting into the abovementioned compensatory wider gait and compensatory trunk movements by the amputee during walking.

BRIEF DESCRIPTION OF THE DRAWINGS

Various embodiments of the invention will be apparent from and elucidated with reference to the embodiments described hereinafter by way of non-limiting examples only and with reference to the schematic figures in the enclosed drawings.

DETAILED DESCRIPTION

Figure 1A:
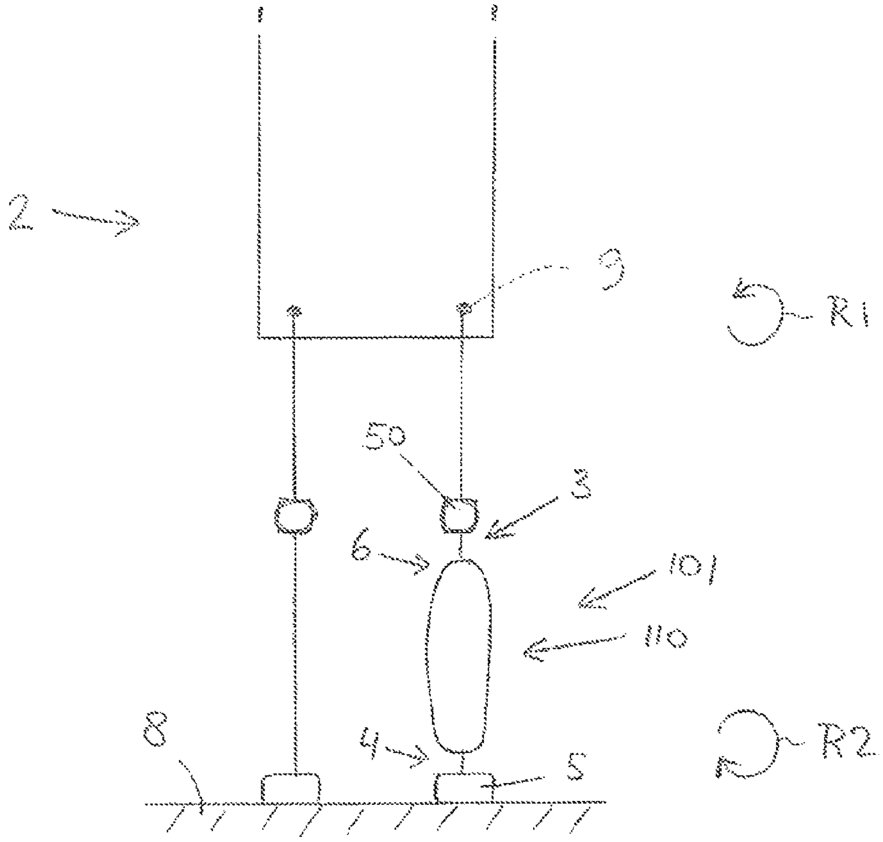
FIGS. 1A and 1B show front schematic views of an embodiment of a prosthesis during use by an amputee standing on a floor.

An embodiment of the invention includes a prosthetic solution according to which lateral balance of upper or lower leg amputees is substantially improved during standing and walking.

An embodiment of the invention includes a lower leg prosthesis for an amputee who has at least one leg having a leg stump. The lower leg prosthesis has a distal end, connectable to an artificial foot, and a proximal end, connectable to said leg stump via a stump socket. A use condition of the lower leg prosthesis includes the distal end being connected to said artificial foot, the proximal end being connected to said leg stump of said amputee via said stump socket. The lower leg prosthesis includes a mechanism which is configured such that, in the use condition of the prosthesis and in an upright position of said amputee with said artificial foot in contact with a floor and in response to a rotative movement of said leg stump around its corresponding hip joint by the amputee with said artificial foot still in contact with the floor, said rotative movement being at least in a frontal plane of the amputee and in a first rotation direction within the frontal plane, the lower leg prosthesis rotates the artificial foot relative to the floor in a second rotation direction within the frontal plane. The first rotation direction is opposite the second rotation direction.

In an embodiment, the rotative movement in the frontal plane of said leg stump around the hip joint is fully controllable from the hip muscles which are typically still available both in upper and lower leg amputees. The rotative movement of the artificial foot in the second direction, while still in contact with the floor, results in a lateral shifting of the center of pressure exerted by the artificial foot on the floor. It also results in a change of the ground reaction force acting on the shifted center of pressure, and in particular, it results in a change of a horizontal component of that ground reaction force in the frontal plane. Controlling this horizontal ground reaction force is a factor in controlling lateral balance of the amputee.

With a lower leg prosthesis according to the embodiment, the amputee is able to control the horizontal ground reaction force and thereby his or her lateral balance by performing a controlled movement with his or her still available hip muscles. Thus the embodiment provides improved lateral balance and reduced energy consumption during standing and walking. This results for example in an improved gait pattern requiring less compensatory trunk movements and allows a more narrow gait to solve balance problems in the frontal plane of the amputee.

The mechanism that implements said rotating of the artificial foot responsive to said rotative movement of the leg stump may configured in various ways, for example by means of various bar mechanisms and/or cylinder-piston configurations, whether or not motor driven and/or electronically controlled, or the like.

However, the abovementioned prosthesis known from EP1340478A2 does not include such a mechanism being arranged for causing such a responsive, oppositely directed rotative movement of the artificial foot relative to the floor on which it rests. Instead, in view of the aim to realize high degree of pivoting freedom at the artificial ankle joint, the prosthesis known from EP1340478A2 has deliberately been designed such that the artificial foot, in response to an amputee performing various tilting movements of the prosthetic lower leg, does not rotate at all relative to the floor on which it rests.

Specific embodiments of the invention are set forth in the appended dependent claims.

The mechanism may be configured to reduce or prevent, during said rotative movement of said leg stump and said responsive rotating of said artificial foot still resting on the floor, the occurrence of loss of height of the hip joint relative to the floor, at least when said rotative movement of said leg stump around the hip joint, as seen in the frontal plane, is unidirectionally performed over at least five degrees in said one rotation direction starting from a position in which the leg stump is vertically extended under the hip joint, and at least when said rotative movement of said leg stump around the hip joint, as seen in the frontal plane, is unidirectionally performed over at least five degrees in said other, i.e. opposite, rotation direction starting from said position in which the leg stump is vertically extended under the hip joint. This prevention of the occurrence of loss of height of the hip joint relative to the floor reduces slight imbalances originating from slight losses of height that would occur due to said rotative movement of said leg stump. Instead of the mechanism being configured for such prevention when such rotative movement is performed over the said at least five degrees in each of both rotation directions, in alternative implementations the mechanism is configured for such prevention when such rotative movement is performed over at least ten degrees in each of both rotation directions. In another implementation, the mechanism is configured for such prevention when such rotative movement is performed over at least twenty degrees in each of both rotation directions.

The implementation for providing the prevention of the occurrence of loss of height of the hip joint relative to the floor may configured in various ways, for example by various bar mechanisms and/or cylinder-piston configurations, whether or not motor driven and/or electronically controlled, or the like.

The abovementioned prosthesis known from EP1340478A2 does not include such a mechanism being arranged for said prevention of the occurrence of loss of height of the hip joint relative to the floor. Instead, for the prosthesis known from EP1340478A2 it is clear that in all tilting positions of the prosthetic lower leg, such as those shown in FIGS. 5A, 5B, 6A, 6B, 7A and 7B of EP1340478A2, there definitely has occurred loss of height of the hip joint relative to the floor as compared to the upright position of the prosthetic lower leg shown in FIGS. 3A and 3B of EP1340478A2.

In an embodiment, the mechanism is a planar hinging bar mechanism having a hinging bar plane which in the use condition is parallel to the frontal plane of the amputee. The planar hinging bar mechanism may include at least nine bars extending parallel to the hinging bar plane and hingedly interconnected with one another via at least six hinge axes extending perpendicular to the hinging bar plane. The at least nine bars may include a first bar, a second bar, a third bar, a fourth bar, a fifth bar, a sixth bar, a seventh bar, an eighth bar and a ninth bar. The at least six hinge axes may include a first hinge axis, a second hinge axis, a third hinge axis, a fourth hinge axis, a fifth hinge axis and a sixth hinge axis.

As seen in said hinging bar plane, in a zero position of the planar hinging bar mechanism the first hinge axis, the second hinge axis, the third hinge axis and the fourth hinge axis are spaced from one another on a straight line, indicated as zero line, with the second hinge axis between the first hinge axis and the third hinge axis and with the third hinge axis between the second hinge axis and the fourth hinge axis. The fifth hinge axis is on one side of the zero line at an orthogonal lateral distance from a portion of the zero line between the third hinge axis and the fourth hinge axis. The sixth hinge axis is on the other, opposite side of the zero line at orthogonal lateral distance from said portion of the zero line.

The at least nine bars may be hingedly interconnected with one another via the at least six hinge axes. For example, the first bar is hingedly connected to the first hinge axis and to the second hinge axis, the second bar is hingedly connected to the second hinge axis and to the third hinge axis, the third bar is hingedly connected to the third hinge axis and to the fourth hinge axis, the fourth bar is hingedly connected to the first hinge axis and to the fifth hinge axis, the fifth bar is hingedly connected to the first hinge axis and to the sixth hinge axis, the sixth bar is hingedly connected to the fifth hinge axis and to the fourth hinge axis, the seventh bar is hingedly connected to the sixth hinge axis and to the fourth hinge axis, the eighth bar is hingedly connected to the fifth hinge axis and to the third hinge axis, and the ninth bar is hingedly connected to the sixth hinge axis and to the third hinge axis.

In an embodiment, each bar of said first, second, fourth, fifth, sixth, seventh, eighth, and ninth bars may include non-sliding connections relative to its corresponding hinge axes. The third bar may include a sliding connection to only one of the third hinge axis or the fourth hinge axis. The slidable connection allows sliding of the third bar relative to said only one hinge axis back and forth in a sliding direction. The sliding direction extends in the hinging bar plane, through the third hinge axis and the fourth hinge axis.

In an embodiment, ends of the first bar and the third bar may include said proximal end and said distal end, respectively, or the ends of the first and the third bar may include said distal end and said proximal end, respectively.

With such a planar hinging bar mechanism, said rotative movement of said leg stump with said artificial foot in contact with the floor causes the hinging bar mechanism to hinge, during which hinging the changing angle between the first bar and the third bar causes said rotating of said artificial foot, still in contact with the floor, responsive to said rotative movement of said leg stump. Furthermore, during said hinging of the hinging bar mechanism, a distance between the third hinge axis and the fourth hinge axis automatically adjusts, which is allowed by said slidable connection of the third bar, so as to reduce or prevent the occurrence of loss of height of the hip joint relative to the floor.

An embodiment of the planar hinging bar mechanism provides the advantages that it is reliable, compact, lightweight, as well as easy to manufacture and repair. It does not require to be motor driven or electronically controlled.

In an embodiment, in said zero position and as seen in said hinging bar plane, the positions of the fifth hinge axis and the sixth hinge axis are mutual mirror image positions relative to the straight line. Such a symmetry promotes that the extent of said responsive counter-rotation of the artificial foot is similar for both directions of rotation of the leg stump around the hip joint in the frontal plane.

In an embodiment, as seen in the hinging bar plane, a distance between the fourth hinge axis and the fifth hinge axis is larger than a distance between the fifth hinge axis and the third hinge axis. Such a property promotes an effective and substantial responsive rotation of the foot.

In an embodiment, at least one of the first bar, the second bar, the third bar, the fourth bar, the fifth bar, the sixth bar, the seventh bar, the eighth bar, or the ninth bar is length adjustable into different lockable lengths. Such adjustability allows for easily adjusting the characteristics of the prosthesis based on an amputee's wishes and/or needs. The adjustability also enables the manufacture of more or less standardized prostheses which may easily be made individually applicable to various dimensions of amputees, leg stumps, artificial feet or artificial knees.

Reference is first made to the embodiment shown in FIGS. 1A through 2B. FIGS. 1A and 2A show amputee 2 standing in an upright position with feet of both legs resting on floor 8. The amputee 2 has a left leg (in FIGS. 1A and 2A shown on the right hand side) having a lower leg stump 3 below a natural knee 50 of the amputee 2. The lower leg prosthesis 101 is shown schematically in its use condition, in which a distal end 4 of the lower leg prosthesis 101 has an artificial foot 5. A proximal end 6 of the lower leg prosthesis 101 forms a stump socket (the stump socket is not shown in detail in FIGS. 1A through 2B), and the stump socket is connected to said leg stump 3. The other, right leg (in FIGS. 1A and 2A shown on the left hand side) of the amputee 2 is completely natural, i.e. it does not have a leg prosthesis.

The lower leg prosthesis 101 comprises a mechanism 110 which is configured such that, in response to the amputee 2 performing a rotative movement (R1) of the leg stump 3 around his or her hip joint 9 of the left leg while keeping the artificial foot 5 resting on the floor 8, said rotative movement at least occurring in a frontal plane of the amputee 2 and in one rotation direction within the frontal plane, the lower leg prosthesis 101 causes said artificial foot 5 to rotate relative to the floor 8 at least in the other, i.e. opposite, rotation direction (R2) within the frontal plane.

The mechanism 110 has only been shown in schematic form in FIGS. 1A through 2B. The reason is that the functions of the mechanism 110 may in principle be implemented by various structural components, many of which will be readily apparent for the skilled person, once the functions of the mechanism have been described herein. However, additional embodiments for the functions of the mechanism 110 will be discussed later on with reference to further specific embodiments as illustrated with reference to FIGS. 3-6.

In FIG. 1A no such rotative movement has yet been carried out, thus the mechanism 110 is in a "zero position". In the zero position the artificial foot 5 is resting on (e.g., is in contact with) the floor 8 with a bottom face of its sole substantially in parallel contact with the floor 8.

Figure 1B:
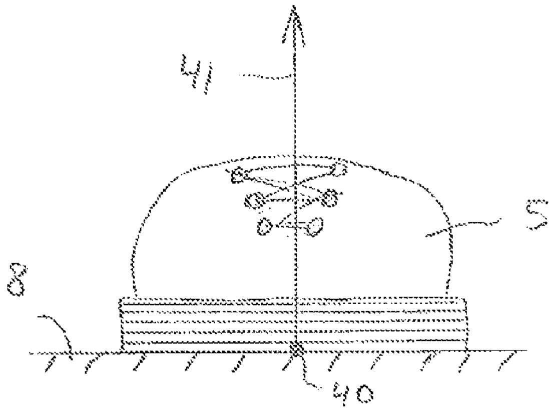

FIG. 1B shows the artificial foot 5 in this condition in an enlarged view. In FIG. 1B there is shown the ground reaction force 41 in the frontal plane which acts on a center of pressure 40. This ground reaction force 41 is substantially vertically directed, it has substantially no horizontal component.

Figure 2A:
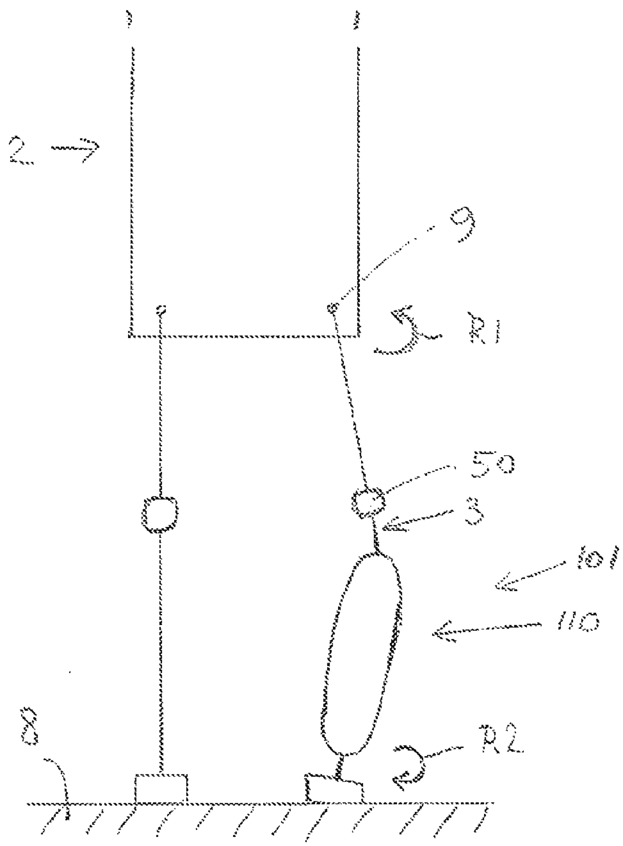
FIGS. 2A and 2B show front schematic views of the embodiment of FIG. 1 in a condition in which the amputee has performed, relative to the condition shown in FIG. 1, a rotative movement of the leg stump around its corresponding hip joint with the artificial foot in contact with the floor, said rotative movement occurring in the shown frontal plane of the amputee.
Figure 2B:
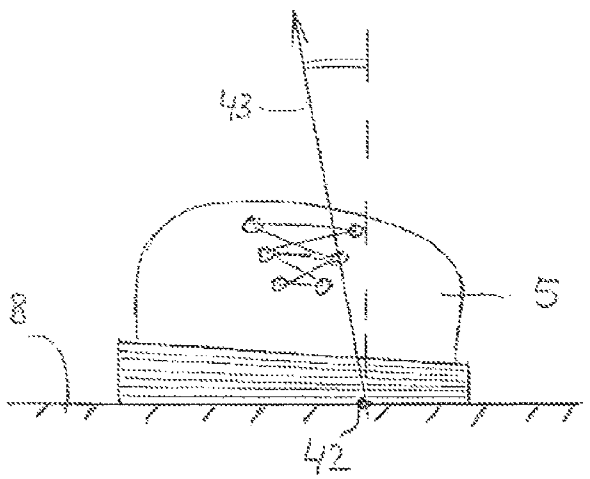

FIG. 2 shows a situation after such rotative movement has been carried out. Therefore, in FIG. 2A the mechanism 110 is not in its zero position anymore. In this position the artificial foot 5 is still resting on the floor 8. Starting off from the zero position in FIG. 1, in FIG. 2 a rotative movement of the leg stump 3 around the hip joint 9 has been carried out in the anti-clockwise rotation direction, indicated in FIGS. 1A and 2A as R1, within the frontal plane. Responsive to that anti-clockwise rotation R1 of the leg stump 3, the lower leg prosthesis 101 has caused artificial foot 5 to rotate relative to the floor 8 in clockwise direction, indicated in FIGS. 1A and 2A as R2, within the frontal plane. In the example of FIGS. 1A through 2B, the amputee 2 has kept the lateral position (within the frontal plane) of the hip joint 9 relative to the artificial foot 5 unaltered during the performing of the rotative movement of the leg stump 3 around the hip joint 9. This can be seen in FIGS. 1A and 2A.

FIG. 2B shows the artificial foot 5 in the rotated condition in an enlarged view. In FIG. 2B there is shown a ground reaction force 43 in the frontal plane considered to be acting on a shifted center of pressure 42. As shown, the position of the shifted center of pressure 42 in FIG. 2 has shifted relative to the position of the center of pressure 40 in FIG. 1 in a horizontal direction that faces away from the other, natural leg. Contrary to the ground reaction force 41 in FIG. 1, the ground reaction force 43 in FIG. 2B has a substantial horizontal component. Note, that in FIG. 2B the sole of foot 5 has been shown in an elastically deformed condition due to the rotation of the foot 5 in the clockwise direction R2.

Conversely, responsive to a clockwise rotation of the leg stump 3, the lower leg prosthesis 101 will cause artificial foot 5 to rotate in anti-clockwise direction. In that case the center of pressure will shift relative to the position of the center of pressure 40 in FIG. 1 in a horizontal direction that faces towards the other, natural leg.

Hence, despite the fact that the amputee 2 lacks neuromechanical control in the lower leg due to a missing natural lower leg, the amputee 2 is able to control, thanks to the lower leg prosthesis 101, the horizontal ground reaction force and thereby his or her lateral balance by performing a controlled movement with his or her still available hip muscles. By varying the extent and/or direction of the controlled movements with the hip muscles, the amputee 2 is able to accurately control his or her lateral balance in a very natural way.

The mechanism 110 may furthermore be configured to reduce or prevent, during certain rotative movements of the leg stump 3 and the responsive rotating of the artificial foot 5 still resting on the floor, the occurrence of loss of height of the hip joint 9 relative to the floor 8. For example, the mechanism 110 may be configured to prevent a loss of height when such rotative movement of said leg stump 3 around the hip joint 9, as seen in the frontal plane, is unidirectionally performed over at least five degrees in said one rotation direction starting from a position in which the leg stump is extending vertically under the hip joint. In another example, the mechanism 110 may be configured to prevent a loss of height when such rotative movement of said leg stump 3 around the hip joint 9, as seen in the frontal plane, is unidirectionally performed over at least five degrees in said other, i.e. opposite, rotation direction starting from said position in which the leg stump 3 is extending vertically under the hip joint. Note that FIG. 1 shows the said position in which the leg stump 3 is vertically extended under the hip joint 9. This prevention of the occurrence of loss of height of the hip joint 9 relative to the floor 8 reduces slight imbalances originating from slight losses of height that would occur due to said rotative movement of said leg stump 3. This function of the mechanism 110 may in principle be implemented by means of various structural components, many of which will be readily apparent for the skilled person, once this function of the mechanism has been described herein. For this reason, FIGS. 1A through 2B do not specifically show such structural components. However, embodiments for realizing this function of the mechanism in structural terms will be discussed below with reference to further specific embodiments as illustrated with reference to FIGS. 3-6.

Reference is now made to an embodiment of a prosthesis 1 shown in FIGS. 3-6. This prosthesis 1 and its planar hinging bar mechanism 10 comprise an embodiment of the lower leg prosthesis 101 and its mechanism 110, respectively, of FIGS. 1A through 2B. With the prosthesis 1 and its planar hinging bar mechanism 10 there can be performed at least the same operational functions as the more generally described operational functions that can be performed with the lower leg prosthesis 101 and its mechanism 110 of FIGS. 1A through 2B. For that reason, some parts and aspects of the prosthesis 1 of FIGS. 3-6 have been indicated with the same reference signs as used for corresponding parts and aspects of the prosthesis 101 of FIGS. 1A through 2B. For simplicity, the floor 8 has been omitted in FIGS. 3-6 and the hip joint 9 has been indicated only in FIG. 6.

The planar hinging bar mechanism 10 comprises first bar 11, second bar 12, third bar 13, fourth bar 14, fifth bar 15, sixth bar 16, seventh bar 17, eighth bar 18 and ninth bar 19, first hinge axis 21, second hinge axis 22, third hinge axis 23, fourth hinge axis 24, fifth hinge axis 25 and sixth hinge axis 26.

The first bar 11 is hingedly connected to the first hinge axis 21 and to the second hinge axis 22. The second bar 12 is hingedly connected to the second hinge axis 22 and to the third hinge axis 23. The third bar 13 is hingedly connected to the third hinge axis 23 and to the fourth hinge axis 24. The fourth bar 14 is hingedly connected to the first hinge axis 21 and to the fifth hinge axis 25. The fifth bar 15 is hingedly connected to the first hinge axis 21 and to the sixth hinge axis 26. The sixth bar 16 is hingedly connected to the fifth hinge axis 25 and to the fourth hinge axis 24. The seventh bar 17 is hingedly connected to the sixth hinge axis 26 and to the fourth hinge axis 24. The eighth bar 18 is hingedly connected to the fifth hinge axis 25 and to the third hinge axis 23. The ninth bar 19 is hingedly connected to the sixth hinge axis 26 and to the third hinge axis 23.

The connection of the third bar 13 to the third hinge axis 23 is a slidable connection 30 that allows sliding of the third bar 13 relative to the third hinge axis 23 back and forth in a sliding direction S1 extending, in a hinging bar plane through the third hinge axis 23 and the fourth hinge axis 24. In the shown example, the slidable connection 30 comprises a slot in the third bar 13, the slot being indicated in a black-filled manner in FIGS. 3 and 5. The third hinge axis 23 is slidable in said slot. Alternatively, i.e. instead of arranging the planar hinging bar mechanism 10 such that the connection of the third bar 13 to the third hinge axis 23 is such a slidable connection, the planar hinging bar mechanism 10 may also be arranged such that the connection of the third bar 13 to the fourth hinge axis 24 is such a slidable connection allowing sliding of the third bar 13 relative to the fourth hinge axis 24 back and forth in said sliding direction S1. In this case the fourth hinge axis 24 may be slidable in a corresponding slot in the third bar 13.

In the shown example, an end of the first bar 11 is in the form of the stump socket 7 and therefore comprises the proximal end 6 of the prosthesis 1, whereas an end of the third bar 13 is in the form of the artificial foot 5 and therefore comprises the distal end 4 of the prosthesis 1. As an alternative embodiment, the planar hinging bar mechanism 10 may be arranged upside-down relative to the shown example. For example, an end of the first bar 11 may comprise the artificial foot 5 and therefore comprises the distal end 4 of the prosthesis 1, whereas an end of the third bar 13 may comprise the stump socket 7 and therefore comprises the proximal end 6 of the prosthesis 1.

With such a planar hinging bar mechanism 10, a rotative movement R1 of the leg stump 3 around the hip joint 9, while keeping the artificial foot 5 resting on the floor 8, causes the planar hinging bar mechanism 10 to hinge, during which hinging a changing angle between the first bar 11 and the third bar 13 causes rotative movement R2 of the artificial foot 5 relative to the floor 8. The rotative movement R2 of the artificial foot 5 allows the artificial foot 5 to rest on the floor 8 through the rotative movement R1 of the leg stump 3. As indicated in FIGS. 3, 5 and 6, the rotative movement R2 of the artificial foot 5 relative to the floor 8 is a counter-rotation as compared to the rotative movement R1 of the leg stump 3.

Furthermore, during said hinging of the planar hinging bar mechanism 10, planar hinging bar mechanism 10 is configured to automatically adjust a distance between the third hinge axis 23 and the fourth hinge axis 24, which is allowed by said slidable connection 30 of the third bar 13, so as to prevent the occurrence of loss of height of the hip joint 9 (see FIGS. 1A through 2B) relative to the floor 8.

Figure 3:
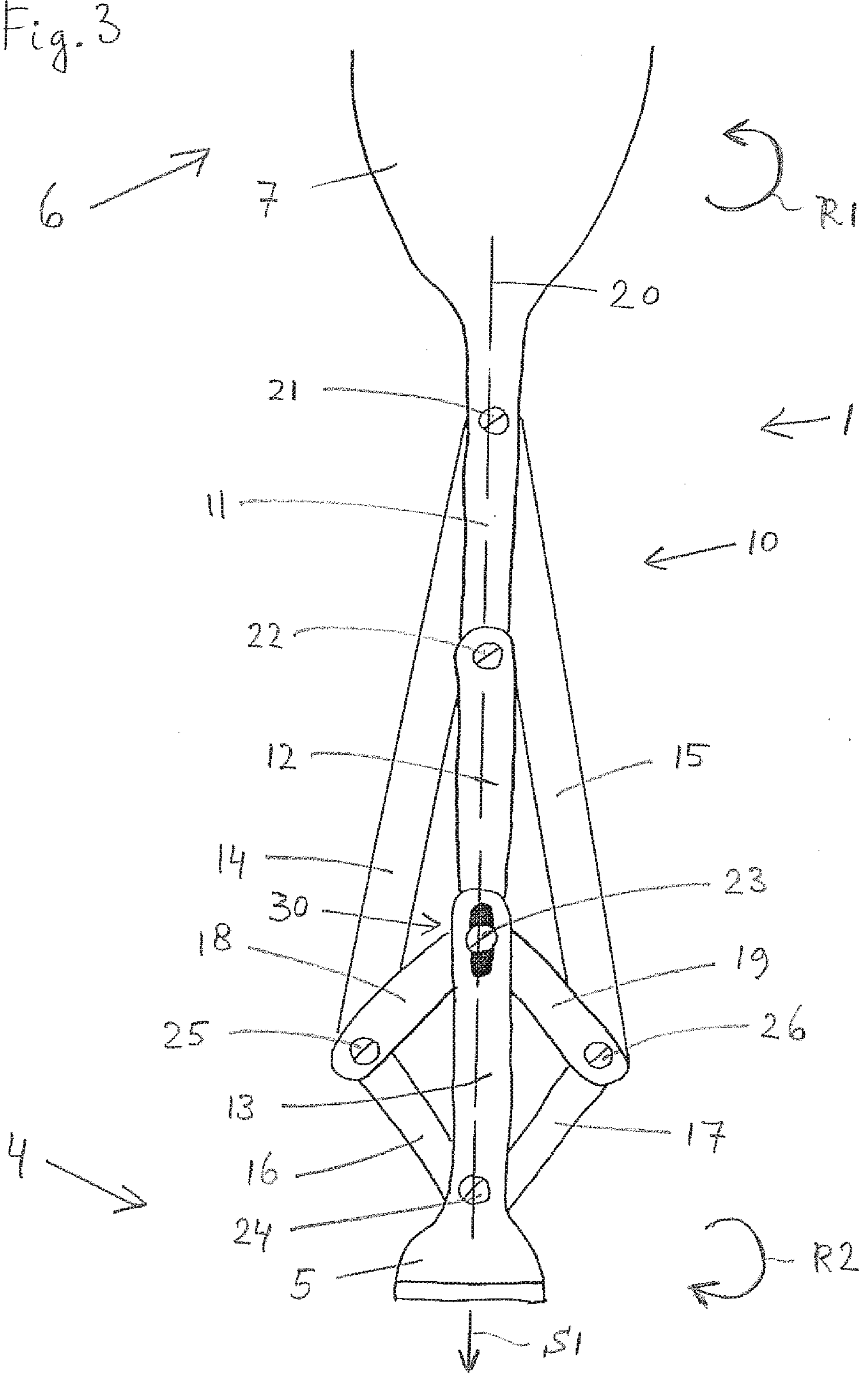
FIG. 3 shows a front schematic view of another embodiment of the prosthesis of FIG. 1 that includes a planar hinging bar mechanism in its zero position.
Figure 4:
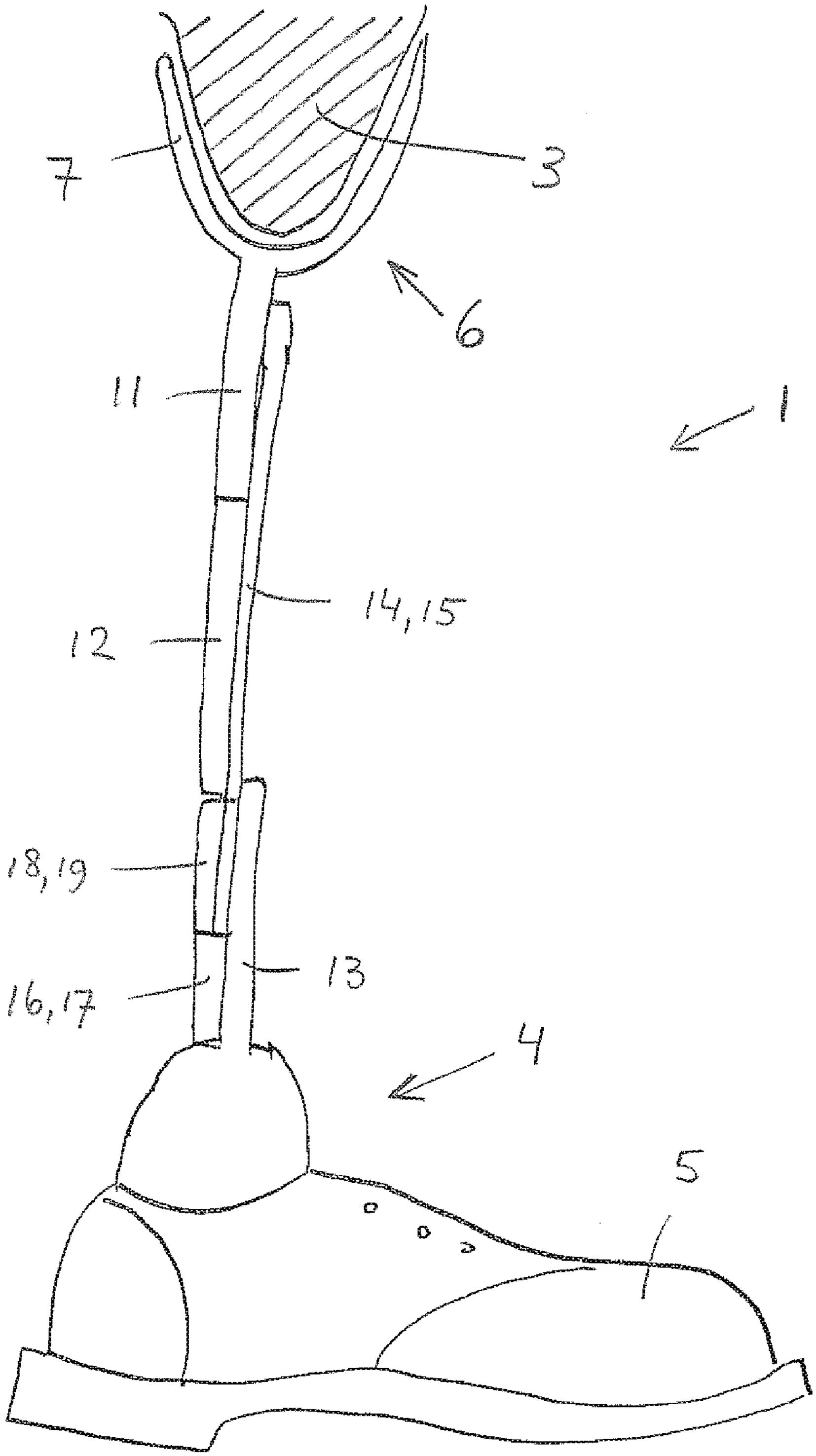
FIG. 4 shows the embodiment of FIG. 3 in side view, i.e. in the sagittal plane of the amputee.
Figure 5:
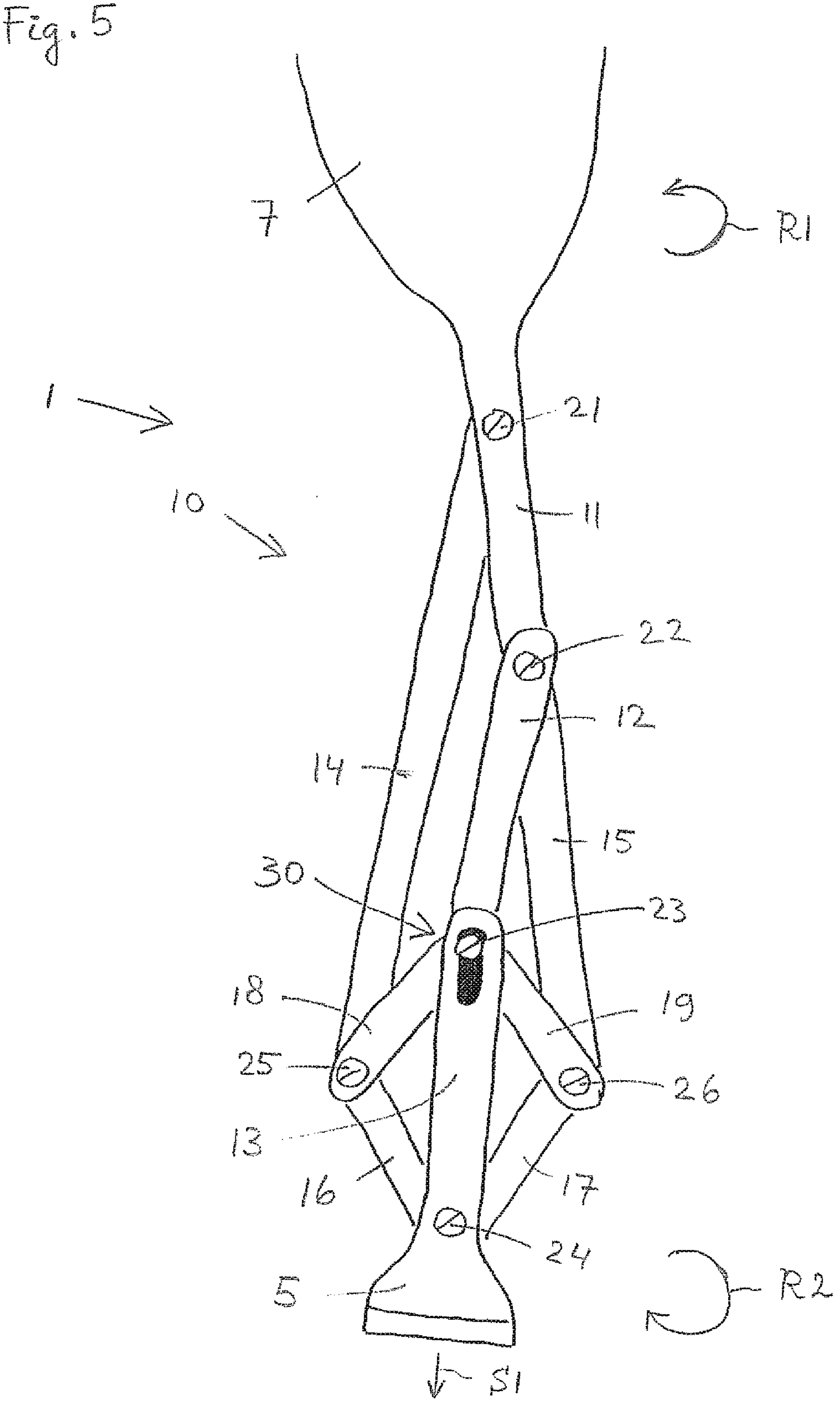
FIG. 5 shows a front schematic view of the embodiment of FIG. 3 in a condition in which the amputee has performed, relative to the condition shown in FIG. 3, a rotative movement of the leg stump, similar to the rotative movement as performed in the embodiment of FIG. 2.
Figure 6:
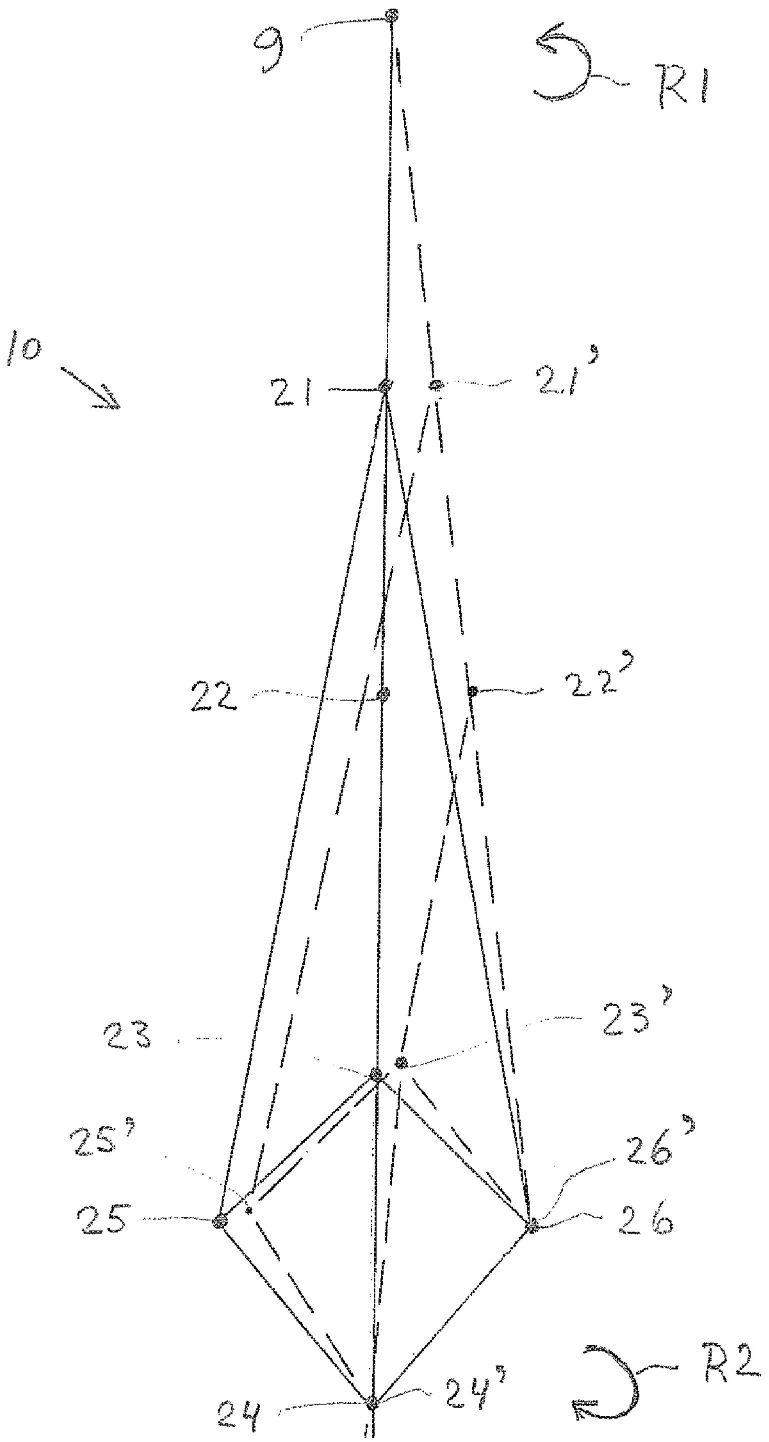
FIG. 6 shows a front schematic view of hinge axes and center lines of bars of the planar hinging bar mechanism of FIG. 3, where the solid lines indicate center line positions of the bars as shown in the condition of FIGS. 3 and 4, and the dashed lines indicate center line positions of the bars as shown in FIG. 5.

These aspects are shown in FIG. 6 which shows, in schematic form, the hinge axes 21-26 and center lines of bars 11-19 of the planar hinging bar mechanism 10 of FIGS. 3, 4 and 5. In FIG. 6, the solid lines indicate positions of the bars 11-19 as shown in the zero position of FIG. 3 whereas the dashed lines indicate positions of the bars 11-19 as shown in the hinged condition of FIG. 5. For clarity, the positions of the hinge axes 21-26 as occurring in the hinged condition of FIG. 5 have been indicated in FIG. 6 by appending an apostrophe after the respective reference numerals. Hence, in FIG. 6 these positions of the hinge axes in said hinged condition have been indicated by the reference signs 21'-26', respectively. Note that also the position of the hip joint 9 (see FIGS. 1A through 2B) has been indicated in FIG. 6. In FIG. 6, the solid line and the dashed line that each correspond to the first bar 11 have been drawn extended to this hip joint 9.

FIG. 6 shows that the dashed line between the points 23' and 24' (this dashed line corresponds to part of the third bar 13) is at an angle to the dashed line between the points 21' and 22' (this dashed line corresponds to part of the first bar 11). From FIG. 6 it also follows that the distance between the points 23' and 24' is larger than the distance between the points 23 and 24. This change of distance corresponds to the abovementioned automatic adjustment allowed by the slidable connection 30 of the third bar 13, so as to prevent the occurrence of loss of height of the hip joint 9 (see FIGS. 1A through 2B) relative to the floor 8.

The embodiment of the planar hinging bar mechanism 10 shown provides the advantages that it is reliable, compact, lightweight, as well as easy to manufacture and repair. The embodiment is not required to be motor driven or electronically controlled.

In the shown example, in said zero position and as seen in said planar hinging bar mechanism 10, the positions of the fifth hinge axis 25 and the sixth hinge axis 26 have mutual mirror image positions relative to a straight line, e.g., zero line 20 (see FIG. 3). Such symmetry promotes that the extent of said responsive counter-rotation of the artificial foot 5 is similar for both directions of rotation of the leg stump 3 around the hip joint 9 in the frontal plane.

Also, in the shown example, as seen in the planar hinging bar mechanism 10, the distance between the fourth hinge axis 24 and the fifth hinge axis 25 is larger than the distance between the fifth hinge axis 25 and the third hinge axis 23. Such a property promotes an effective and substantial responsive rotation of the foot 5.

At least one of the first bar 11, the second bar 12, the third bar 13, the fourth bar 14, the fifth bar 15, the sixth bar 16, the seventh bar 17, the eighth bar 18, the ninth bar 19 may be length adjustable into different lockable lengths. Such adjustability allows for easily adapting the characteristics of the prosthesis 1 based on an amputee's wishes and/or needs. The adjustability also promotes the manufacture of generally standardized prostheses which may be more easily made individually applicable to various dimensions of amputees, leg stumps, artificial feet or artificial knees.

In the foregoing specification, the invention has been described with reference to specific examples of embodiments of the invention. It will, however, be evident that various modifications and changes may be made therein without departing from the broader scope of the invention as set forth in the appended claims.

For instance, in the shown examples, the amputee 2 has a natural knee with a lower leg stump and the prosthesis is connected with a stump socket to this lower leg stump. However, the prosthesis according to another embodiment of the invention may be arranged such that in its use condition the stump socket is interposed between an upper leg stump and an artificial knee. Such an artificial knee may be part of or connectable to the prosthesis according to the invention.

However, other modifications, variations and alternatives are also possible. The specifications and drawings are, accordingly, to be regarded in an illustrative rather than in a restrictive sense.

The invention claimed is:

1. A lower leg prosthesis for an amputee who has at least one leg having a leg stump, the lower leg prosthesis comprising:

a distal end connectable to an artificial foot; and a proximal end connectable to said leg stump via a stump socket;

wherein a use condition of the lower leg prosthesis includes the distal end being connected to said artificial foot, the proximal end being connected to said leg stump of said amputee via said stump socket;

wherein the lower leg prosthesis further comprises a mechanism which is configured such that, in said use condition of the lower leg prosthesis and in an upright position of said amputee with said artificial foot in contact with a floor and in response to a rotative movement of said leg stump around its corresponding hip joint by the amputee with said artificial foot still in contact with the floor, said rotative movement being at least in a frontal plane of the amputee and in a first rotation direction within the frontal plane, the lower leg prosthesis rotates the artificial foot relative to the floor in a second rotation direction within the frontal plane;

wherein the first rotation direction is opposite the second rotation direction.

2. A lower leg prosthesis according to claim 1, wherein said mechanism is further configured to reduce, during said rotative movement of said leg stump and said responsive rotation of said artificial foot, the occurrence of loss of height of the hip joint relative to the floor, at least when said rotative movement of said leg stump around the hip joint is unidirectionally performed over at least five degrees in said first rotation direction starting from a position in which the leg stump is vertically extended under the hip joint, and at least when said rotative movement of said leg stump around the hip joint is unidirectionally performed over at least five degrees in said second rotation direction starting from said position in which the leg stump is vertically extended under the hip joint.

3. A lower leg prosthesis according to claim 1, wherein the mechanism is a planar hinging bar mechanism having a hinging bar plane which in the use condition is parallel to the frontal plane of the amputee, wherein the planar hinging bar mechanism comprises at least nine bars that extend parallel to the hinging bar plane and are hingedly interconnected with one another via at least six hinge axes that extend perpendicular to the hinging bar plane, wherein the at least nine bars comprise a first bar, a second bar, a third bar, a fourth bar, a fifth bar, a sixth bar, a seventh bar, an eighth bar, and a ninth bar, wherein the at least six hinge axes comprise a first hinge axis, a second hinge axis, a third hinge axis, a fourth hinge axis, a fifth hinge axis, and a sixth hinge axis;

wherein in a zero position of the planar hinging bar mechanism:

the first hinge axis, the second hinge axis, the third hinge axis and the fourth hinge axis are spaced from one another on a straight line, with the second hinge axis between the first hinge axis and the third hinge axis and with the third hinge axis between the second hinge axis and the fourth hinge axis, the fifth hinge axis is on one side of the straight line at an orthogonal lateral distance from a portion of the straight line that is between the third hinge axis and the fourth hinge axis, and the sixth hinge axis is on an opposite side of the straight line at the orthogonal lateral distance from said portion of the straight line;

wherein the first bar is hingedly connected to the first hinge axis and to the second hinge axis, the second bar is hingedly connected to the second hinge axis and to the third hinge axis, the third bar is hingedly connected to the third hinge axis and to the fourth hinge axis, the fourth bar is hingedly connected to the first hinge axis and to the fifth hinge axis, the fifth bar is hingedly connected to the first hinge axis and to the sixth hinge axis, the sixth bar is hingedly connected to the fifth hinge axis and to the fourth hinge axis, the seventh bar is hingedly connected to the sixth hinge axis and to the fourth hinge axis, the eighth bar is hingedly connected to the fifth hinge axis and to the third hinge axis, and the ninth bar is hingedly connected to the sixth hinge axis and to the third hinge axis;

wherein each bar of said first, second, fourth, fifth, sixth, seventh, eighth, and ninth bars comprises non-sliding connections relative to its corresponding hinge axes;

wherein said third bar comprises a sliding connection to only one of the third hinge axis or the fourth hinge axis;

wherein the slidable connection allows sliding of the third bar relative to said only one hinge axis back and forth in a sliding direction;

wherein the sliding direction extends in the hinging bar plane, through the third hinge axis and the fourth hinge axis; and wherein ends of the first bar and the third bar comprise one of:

said proximal end and said distal end of the prosthesis, respectively, or said distal end and said proximal end, respectively.

4. A lower leg prosthesis according to claim 3, wherein, in said zero position, the positions of the fifth hinge axis and the sixth hinge axis are mutual mirror image positions relative to the straight line.

5. A lower leg prosthesis according to claim 3, wherein a distance between the fourth hinge axis and the fifth hinge axis is larger than a distance between the fifth hinge axis and the third hinge axis.

6. A lower leg prosthesis according to claim 3, wherein at least one of the first bar, the second bar, the third bar, the fourth bar, the fifth bar, the sixth bar, the seventh bar, the eighth bar, or the ninth bar is length adjustable into different lockable lengths.

7. A lower leg prosthesis according to claim 4, wherein a distance between the fourth hinge axis and the fifth hinge axis is larger than a distance between the fifth hinge axis and the third hinge axis.

8. A lower leg prosthesis according to claim 4, wherein at least one of the first bar, the second bar, the third bar, the fourth bar, the fifth bar, the sixth bar, the seventh bar, the eighth bar, or the ninth bar is length adjustable into different lockable lengths.

9. A lower leg prosthesis according to claim 5, wherein at least one of the first bar, the second bar, the third bar, the fourth bar, the fifth bar, the sixth bar, the seventh bar, the eighth bar, or the ninth bar is length adjustable into different lockable lengths.

10. A lower leg prosthesis according to claim 1, wherein the distal end comprises the artificial foot.

11. A lower leg prosthesis according to claim 1, wherein the proximal end comprises the stump socket.

12. A lower leg prosthesis according to claim 1, wherein the proximal end is connectable via an artificial knee to the stump socket.

* * * * *